United States Patent [19]

Picard-Seon et al.

[11] Patent Number: 5,132,048

[45] Date of Patent: Jul. 21, 1992

[54] WEAKLY ACIDIC COLLOIDAL DISPERSIONS OF CERIUM (IV) COMPOUNDS

[75] Inventors: Françoise Picard-Seon, Fontenay Sous Bois; Robert Zerrouk, Saint Victor Malscours, both of France

[73] Assignee: Rhone-Poulenc Chimie, Courbevoie, France

[21] Appl. No.: 628,368

[22] Filed: Dec. 17, 1990

[30] Foreign Application Priority Data

Dec. 15, 1989 [FR] France .................................. 89 16598

[51] Int. Cl.$^5$ .............................................. B01J 13/00
[52] U.S. Cl. .................... 252/313.1; 252/314; 423/21.5; 423/263; 502/304
[58] Field of Search ............................ 252/314, 313.1; 423/21.5, 263; 502/304

[56] References Cited

U.S. PATENT DOCUMENTS

| | | | |
|---|---|---|---|
| 3,761,571 | 9/1973 | Woodhead | 423/263 |
| 4,181,532 | 1/1980 | Woodhead | 106/40 R |
| 4,356,106 | 10/1982 | Woodhead | 252/313 R |
| 4,699,732 | 10/1987 | Woodhead | 252/314 |
| 4,940,685 | 7/1990 | Sauvion et al. | 502/263 |
| 4,965,057 | 10/1990 | David et al. | 423/263 |
| 5,002,747 | 3/1991 | Le Loarer | 423/592 |
| 5,021,192 | 6/1991 | David et al. | 252/313.1 |

OTHER PUBLICATIONS

Derwent Abstract EP-316205.
Derwent Abstract EP-239477.
Derwent Abstract EP-208581.

*Primary Examiner*—Richard D. Lovering
*Assistant Examiner*—N. Bhat
*Attorney, Agent, or Firm*—Burns, Doane, Swecker & Mathis

[57] ABSTRACT

Weakly acidic colloidal aqueous dispersions of particulates of a cerium (IV) compound, having a pH ranging from 1.5 to 5, well adapted for catalyst applications, are prepared by (a) acidulating a cerium (IV) hydroxide with an acid having a pKa ranging from 2.5 to 5.0, or with a salt or mixture thereof, (b) next separating the resulting cerium (IV) compound that precipitates from the medium of acidulation, and then (c) colloidally dispersing such cerium (IV) precipitate in an aqueous medium.

18 Claims, No Drawings

WEAKLY ACIDIC COLLOIDAL DISPERSIONS OF CERIUM (IV) COMPOUNDS

BACKGROUND OF THE INVENTION

1. Field of the Invention

The present invention relates to novel weakly acidic colloidal dispersions of a cerium (IV) compound in an aqueous medium, and to a process for the preparation of such weakly acidic colloidal dispersions of a cerium (IV) compound.

In the description which follows, a colloidal dispersion of a cerium (IV) compound in an aqueous medium is also designated by the term "sol".

2. Description of the Prior Art

Colloidal dispersions of a cerium (IV) compound are known to this art; they are useful for a wide variety of applications. Moreover, one major application for these dispersions is in heterogeneous catalysis and, in particular, for the catalytic conversion of exhaust gases emanating from internal combustion engines, also termed the catalysis of automotive post-combustion reactions.

Indeed, cerium (IV) is an important promoter of such catalytic activity, in particular because of its capacity for storing oxygen and thus creating an oxygen supersaturation in the vicinity of the catalytically active elements such as platinum, palladium or the like.

For this purpose, the colloidal dispersions are used as a medium for impregnating a support with cerium, with cerium oxide being produced by calcination of the impregnated support and, thus, by decomposition of the cerium (IV) compound contained in the dispersion.

Moreover, the acid nature of the colloidal dispersion influences the support-impregnating process, which must be suited to the characteristics of said support and in particular to its surface properties.

Thus, colloidal dispersions of a cerium (IV) compound, notably a cerium hydroxynitrate, are known to this art and are very highly acidic, typically having a pH of less than 1. These dispersions present numerous problems during impregnation, when the support to be impregnated is slightly basic in nature.

Published European Patent Application No. 316,205, on the other hand, describes the production of such colloidal dispersions which are weakly acidic in nature, generally having a pH higher than 3.5.

This process entails destabilizing an aqueous colloidal dispersion of a cerium hydroxynitrate by an acid having a pKa lower than that of nitric acid, for example by acetic acid.

Such process is also complex, because it comprises the successive production of two colloidal dispersions, a first dispersion by subjecting a hydroxide to attack by nitric acid, followed by a second dispersion by destabilization of the first suspension using acetic acid. Moreover, it requires a significant consumption of reagents such as nitric acid and acetic acid.

SUMMARY OF THE INVENTION

Accordingly, a major object of the present invention is the provision of improved, weakly acidic colloidal dispersions of a cerium (IV) compound by a process that is far simpler and less costly in terms of consumption of reagents than those processes to date characterizing the state of this art.

Briefly, the present invention features the production of a colloidal suspension of a cerium (IV) compound, comprising acidulating, or subjecting a cerium (IV) hydroxide to attack by a solution of an acid or acids having a pKa ranging from 2.5 to 5.0, or of an alkali metal or ammonium salt of such acids, or mixture thereof, next separating off the cerium (IV) compound that precipitates therefrom, and then dispersing such separated compound in water.

DETAILED DESCRIPTION OF THE PREFERRED EMBODIMENTS OF THE INVENTION

More particularly according to the present invention, exemplary such cerium (IV) hydroxides are those produced by precipitation in a basic and oxidizing medium.

Exemplary acids useful for carrying out the process of the invention include, in particular, acetic acid, formic acid, propionic acid and chloroacetic acid. Preferably, acetic acid is used.

It is also possible to use the salts of these acids or a salt/acid mixture. Exemplary of these salts are the alkali metal salts or the ammonium salts. The ammonium salts are the preferred. Indeed, ammonium compounds typically present no problems in catalytic reactions and, on the other hand, will be decomposed during the calcination of the sol in the event that it is desired to obtain an oxide, typically the case in catalysis.

The acid solutions used for the attack can either be a concentrated acid or an aqueous solution thereof. Preferably, the total acid plus acid salt concentration ranges from 1 mole/l to 3 moles/l.

In a preferred embodiment of the invention, the amount of acid added is such that the molar ratio (acid + salt)/cerium (IV) ranges from about 0.5 to about 1.3, preferably from 0.7 to 1.0.

By the term "acid" are intended an acid, a mixture of acids, a salt, a mixture of salts or an acids/salts mixture.

The attack or acidulation of the cerium hydroxide is carried out by simple mixing of this hydroxide with the acid, at a temperature which is not critical. This temperature can be close to ambient temperature (15° C. to 25° C.). Such attack can also be carried out at elevated temperatures, e.g., up to a temperature on the order of 100° C.

The precipitate thus obtained is then separated from the reaction mixture by any suitable means, for example filtration, centrifuging or settling.

The precipitate is then dispersed in water.

The concentration of cerium (IV) contained in the dispersion advantageously ranges from 1 mole/l to 3 moles/l.

The amount of cerium (IV) in peptizable form contained in the dispersion ranges from 50% to 100% of the total amount of cerium, preferably from 95% to 100%.

The colloidal dispersion of the cerium (IV) compound according to this invention has a pH ranging from 1.5 to 5, preferably ranging from 2.5 to 5.

The compound constituting the colloids has the following formula:

$$Ce(A)_x(OH)_{4-x}$$

in which A is the anion of an acid or of a salt of such acid having a pKa ranging from 2.5 to 5.0, and x is a number higher than or equal to 0.01 and less than or equal to 0.7.

This compound may also contain other anions in a small proportion, these anions originating from the hydroxide used as the starting material.

Thus, the compound may contain nitrate anions in a molar proportion, relative to cerium, of less than 0.15, preferably less than 0.10.

The dispersed particles have colloidal dimensions, the average hydrodynamic diameter of which ranges from 8 to 15 nm.

This size is determined by the quasi-elastic diffusion of light in accordance with the technique described by Michael L. MacComwell in *Analytical Chemistry*, Vol. No. 3 No. 8, 1007 (1981).

The average hydrodynamic diameter of the particles depends on the pH of the dispersion. Thus, the colloids are the larger, the higher the pH of the sol.

The sols of the invention are stable under customary storage conditions and are used, in particular, to produce catalysts, for example by impregnation of a support such as alumina with this sol, followed by calcination to generate a cerium oxide.

In order to further illustrate the present invention and the advantages thereof, the following specific examples are given, it being understood that same are intended only as illustrative and in nowise limitative.

EXAMPLE 1

94 ml of 17 N acetic acid and 90 ml of distilled water were added to 340 g of cerium hydroxide.

This mixture was magnetically stirred until a homogeneous suspension was obtained. The pH of the suspension was 1.6. After filtering, the mass of moist hydroxyacetate recovered was 380 g. This precipitate was redispersed in 760 ml of distilled water. The sol produced was stable and had a pH of 1.5. It contained 240 g/l of $CeO_2$. This sol could be concentrated to 500 g/l by evaporation.

EXAMPLE 2

A solution containing 64.7 ml of 17 N acetic acid and 38.5 g of ammonium acetate was added to 340 g of cerium hydroxide. The volume thereof was increased to 1 liter by addition of distilled water. This mixture was magnetically stirred until a homogeneous suspension was obtained. The pH of the suspension was 4.1. After filtering, the mass of moist hydroxyacetate recovered was 380 g. This precipitate was redispersed in 760 ml of distilled water. The sol obtained was stable and had a pH of 4.1. It contained 260 g/l of $CeO_2$.

EXAMPLE 3

340 g of cerium hydroxide were added to a solution containing 82.3 ml of 17 N acetic acid and 15.4 g of ammonium acetate in 1 liter of water.

After stirring, a suspension was obtained and, after filtering and redispersing the precipitate, a sol was obtained which had a pH of 3, containing 255 g/l of $CeO_2$.

This sol could be concentrated by evaporation to a concentration of 500 g/l of $CeO_2$. All of the cerium was in colloidal cerium (IV) form.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A weakly acidic colloidal dispersion of particulates of a cerium (IV) compound, having the formula: $Ce(A)_x(OH)_{4-x}$ in which A is an anion of an acid having a pKa ranging from 2.5 to 5.0, or salt thereof, and x is a number ranging from 0.01 to 0.7 in an aqueous medium, said dispersion having a pH ranging from 1.5 to 5, and the colloidal particulates thereof having an average hydrodynamic diameter ranging from 8 to 15 nm.

2. The colloidal dispersion as defined by claim 1, having a pH ranging from 2.5 to 5.

3. The colloidal dispersion as defined by claim 1, the cerium concentration therein ranging from 1 mole/l to 3 moles/l.

4. The colloidal dispersion as defined by claim 3, wherein the proportion of the cerium (IV) compound in colloidal state ranges from 50% to 100% of the total amount of cerium values contained therein.

5. The colloidal dispersion as defined by claim 4, such proportion ranging from 95% to 100%.

6. The colloidal dispersion as defined by claim 1, further comprising nitrate anions, in a molar proportion, relative to cerium, of less than 0.15.

7. The colloidal dispersion as defined by claim 6, said molar proportion being less than 0.10.

8. The colloidal dispersion as defined by claim 1, wherein the molar ratio (acid+salt)/cerium (IV) ranges from 0.5 to 1.3.

9. The colloidal dispersion as defined by claim 8, said molar ratio ranging from 0.7 to 1.0.

10. A process for the preparation of a weakly acidic colloidal dispersion of particulates of a cerium (IV) compound, having the formula: $Ce(A)_x(OH)_{4-x}$ in which A is an anion of an acid having a pKa ranging from 2.5 to 5.0, or salt thereof, and x is a number ranging from 0.01 to 0.7 in an aqueous medium, said dispersion having a pH ranging from 1.5 to 5, said process comprising (a) acidulating a cerium (IV) hydroxide with an acid having a pKa ranging from 2.5 to 5.0, or with a salt or mixture thereof, (b) next separating the resulting cerium (IV) compound that precipitates from the medium of acidulation, and then (c) colloidally dispersing such cerium (IV) precipitate in an aqueous medium.

11. The process as defined by claim 10, said acid comprising acetic acid, propionic acid, chloroacetic acid or formic acid.

12. The process as defined by claim 11, said acid comprising acetic acid.

13. The process as defined by claim 10, comprising acidulating the cerium (IV) hydroxide with an alkali metal or ammonium salt of said acid.

14. The process as defined by claim 12, comprising acidulating the cerium (IV) hydroxide with an aqueous solution of said acid, or salt or mixture thereof, said solution having a total (acid+salt) concentration ranging from 1 mole/l to 3 moles/l.

15. The process as defined by claim 10, wherein the molar ratio (acid+salt)/cerium (IV) ranges from 0.5 to 1.3 in said acidulating step (a).

16. The process as defined by claim 15, said molar ratio ranging from 0.7 to 1.0.

17. The process as defined by claim 10, comprising acidulating at a temperature ranging from ambient to 100° C.

18. The process as defined by claim 10, further comprising concentrating the colloidal dispersion thus produced.

* * * * *